United States Patent [19]

Archibald et al.

[11] Patent Number: 5,789,617
[45] Date of Patent: Aug. 4, 1998

[54] NEOPENTYL DIFLUOROAMINO COMPOUNDS FOR USE IN ENERGETIC FORMULATIONS

[75] Inventors: Thomas G. Archibald, Fair Oaks; Gerald E. Manser, El Dorado Hills, both of Calif.

[73] Assignee: Aerojet-General Corporation, Sacramento, Calif.

[21] Appl. No.: 939,172

[22] Filed: Sep. 2, 1992

[51] Int. Cl.⁶ .................................................. C07C 211/03
[52] U.S. Cl. .................. 564/121; 564/107; 564/108; 564/109; 564/110; 564/112; 564/113; 564/115; 564/118; 564/121
[58] Field of Search .................. 564/118, 121, 564/107, 109, 110, 112, 113, 115

[56] References Cited

U.S. PATENT DOCUMENTS

| | | | |
|---|---|---|---|
| 3,729,501 | 4/1973 | Rohrback et al. | 564/121 |
| 4,118,414 | 10/1978 | Goldstein et al. | 558/483 |

OTHER PUBLICATIONS

Hafner et al., JACS, 79(14), pp. 3783–3786 (1957).
Wenker, JACS 57(6), pp. 1079–1080 (1935).
Grakauskas et al., J. Org. Chem., 35(5), pp. 1545–1549 (1970).

*Primary Examiner*—Brian M. Burn
*Attorney, Agent, or Firm*—Townsend and Townsend and Crew LLP

[57] ABSTRACT

This invention relates to novel neopentyl difluoroamino compounds which are useful as plasticizers and oxidizers in energetic formulations, such as propellants, explosives, and gasifiers. These neopentyl difluoroamino compounds can be prepared either: (1) by the direct fluorination of amine derivatives containing energetic pendant groups; or (2) by first preparing $NF_2$-derivatives and then substituting these derivatives with energetic pendant groups. In particular, mono- and bis-(difluoroaminomethyl) oxetanes are synthesized and further reacted to yield the corresponding dinitrate esters. It has been discovered that these $NF_2$-dinitrate esters are very useful as energetic plasticizers in high-energy formulations.

10 Claims, No Drawings

NEOPENTYL DIFLUOROAMINO COMPOUNDS FOR USE IN ENERGETIC FORMULATIONS

FIELD OF THE INVENTION

This invention relates to novel neopentyl difluoroamino compounds. The compounds of the present invention are useful as plasticizers and oxidizers in high-energy formulations, such as propellants, explosives, gasifiers, or the like.

BACKGROUND OF THE INVENTION

High-energy solid formulations, such as propellants, explosives, and gasifiers, generally consist of particulate solids, such as fuel material, oxidizers, or both, held together by an elastomeric binder. These high-energy formulations also often include a plasticizer, such as a nitrate ester, which is a liquid prior to its incorporation into the formulation.

Organic compounds which contain nitrogen and fluorine are frequently used as fuel material and/or particulate oxidizers. These compounds are most suitable for making high-energy propellants because such compounds form gaseous HF as a decomposition product. During decomposition, the high heat of formation of HF is liberated to the surroundings, thereby doing mechanical work. Additionally, during the course of decomposition, fluorine is present as an oxidizing agent, and thus, no external source is required to complete oxidation.

Plasticizers are used in solid propellants and explosives to facilitate processing and increase flexibility and toughness, in addition to providing other benefits which vary with the nature and use of the formulation. Energetic or high-energetic plasticizers are those that provide energy in addition to flexibility and toughness, and their inclusion therefore does not lessen the performance of the formulation. Considerations involved in the selection and use of plasticizers include compatibility with the other components of the formulation, including the primary energetic compounds and any binders present, the oxygen balance of the plasticizer, energy content, safety (i.e., stability with regard to detonation), and melting point. Plasticizers with melting points in a range which causes them to crystallize readily, for example, are of limited utility, since crystallization is detrimental to the plasticizer function and can adversely affect the mechanical properties of the propellant or explosive.

While the binder is an important means of maintaining the uniformity of the formulation and of holding it together, the binder material burns with substantially lower energy than the fuel. The binder thus imposes a limit on the energy content of the fuel material. One way of minimizing this limitation is to use a binder which release as much energy as possible when burning with the fuel. It is desirable, therefore, that the elastomeric binder have pendant groups which themselves are relatively high in energy.

Additionally, if a nitroester plasticizer is used in conjunction with the binder, nitroester-miscibility is required. Thus, in addition to being relatively high in energy, the polyethers and the elastomers formed therefrom should contain pendant groups which impart miscibility of the elastomer with the nitrate ester plasticizers. Nitro, nitrato, nitramino and cyano groups are examples of pendant groups which impart nitrate estermiscibility to the polymer and which have relatively high energies so as to contribute to the performance of the propellant.

Compounds containing two fluorine atoms bonded to nitrogen, i.e., a difluoroamino ($NF_2$) group, have been extensively studied as ingredients for propellants and explosives. The difluoroamino group has higher energy, higher positive heat of formation and greater thermal stability than the other frequently used pendant groups (e.g. the nitrato group). In addition to significantly improved energy content, the difluoroamino group strongly enhances the performance of formulations containing boron and aluminum as fuels.

Practical use of the difluoroamino group in propellants and explosives has been limited, however. In compounds known to date, the difluoroamino group was found to impart unacceptably high impact sensitivity or chemical instability to the compound. Due to the strong electron-withdrawing nature of the difluoroamino group, $NF_2$-containing compounds have been found to be unstable and readily lose HF to form nitriles when alpha hydrogens are present. Therefore, the use of $NF_2$-containing compounds in explosives and propellants has been limited to those compounds containing difluoroamino groups on a tertiary center prepared from tetrafluorohydrazine, or geminal di-difluoroamino groups prepared from strong acid solutions of difluoroamine. In both cases the resulting products are shock sensitive and expensive to prepare.

SUMMARY OF THE INVENTION

It has been discovered that when a difluoroamino group is placed on a neopentyl carbon (i.e., a primary carbon directly bonded to a quaternary carbon), compounds are available that have remarkable stability and low impact sensitivity. When an aliphatic $NF_2$ group is located on a neopentyl carbon, there is sufficient steric hinderance to stabilize the $NF_2$ group and prevent liberation of HF. These neopentyl difluoroamino compounds may successfully be used in energetic formulations as oxidizers, plasticizers and elastomeric binders. It has also been discovered that compounds containing neopentyl difluoroamino groups are readily prepared in high yield by the direct fluorination of blocked neopentyl amines.

In particular, the present invention provides a variety of high-energy, neopentyl difluoroamino compounds which are useful as oxidizers and plasticizers in energetic formulations. These neopentyl difluoroamino compounds can be prepared either: (1) by the direct fluorination of amine derivatives containing energetic pendant groups; or (2) by first preparing $NF_2$-derivatives and then substituting these derivatives with energetic pendant groups. More specifically, mono-$NF_2$ and bis-$NF_2$-oxetanes are synthesized and further reacted to yield the corresponding dinitrate esters. It has been discovered that these $NF_2$-dinitrate esters are very useful as energetic plasticizers in high-energy formulations. The plasticizer compounds of the present invention are particularly compatible with binders containing the $NF_2$ group prepared from $NF_2$-containing oxetanes, i.e., from mono-$NF_2$-oxetane and/or bis-$NF_2$-oxetane.

Other advantages, objects, features and embodiments of the present invention will become apparent from the detailed description which follows.

DETAILED DESCRIPTION OF THE INVENTION AND PREFERRED EMBODIMENTS

Neopentyl difluroamino compounds in accordance with the present invention are those having the general formula:

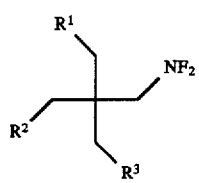

(I)

In Formula I, $R^1$, $R^2$, $R^3$ may be the same or different, and are selected from functional groups including, but not limited to, H, lower alkyl, $NF_2$, $NO_2$, $ONO_2$, $N_3$, or $N(R^4)NO_2$ where $R^4$ is H or a lower alkyl; or $R^1$ and $R^2$ may be combined as a single divalent radical and may be, for example, $-N(NO_2)-$or$-N(NO_2)-CH_2-N(NO_2)-$; and, when $R^1$ and $R^2$ are so combined, $R^3$ may be, for example, $NF_2$, $ONO_2$, $NO_2$, or $N_3$. The term "independently selected" is used in the claims herein to indicate that two or more of the R groups may be identical or all may be different. The term "alkyl" is used herein to refer to substituents which are fully saturated hydrocarbon chains. The alkyl groups may be either straight-chain or branched-chain, limited only by steric hinderance. The term "lower alkyl" is used herein as it is used in the art, designating alkyl groups of a relatively small number of carbon atoms. Additionally, since alkyl groups do not add to the energetic character of the molecule, shorter alkyl groups (i.e., 1–4 carbons) are preferred.

Within the scope of Formula I, certain embodiments are preferred, namely those in which $R^1$, $R^2$, and $R^3$ are the same or different, and are selected from the following functional groups: H, $CH_3$, $C_2H_5$, $NF_2$, $ONO_2$, $NO_2$, $N_3$, $N(CH_3)NO_2$ and $N(C_2H_5)NO_2$. Further preferred are those compounds in which $R^1$, $R^2$, and $R^3$ are selected from the following functional groups: H, $NF_2$ and $ONO_2$. Even more preferred are those compounds in which $R^1$ is either H or $NF_2$; $R^2$ is $ONO_2$; and $R^3$ is $ONO_2$.

The energy content and physical properties of the compounds represented by Formula I vary. Table I lists the properties of several neopentyl-$NF_2$-nitrate plasticizers. Mixtures of these compounds give eutectics with useful plasticizer melting ranges. These compounds are particularly compatible with binders containing the $NF_2$ group prepared from $NF_2$-containing oxetanes, i.e., from mono-$NF_2$-oxetane and/or bis-$NF_2$-oxetane.

group including, but not limited to, H, lower alkyl, $NF_2$, $ONO_2$, $NO_2$, $N_3$ and $N(R^4)NO_2$, where $R^4$ is H or a lower alkyl; $R^2$ is $ONO_2$; and $R^3$ is $ONO_2$. The process of the present invention involves: (a) combining a solution of a compound having the formula:

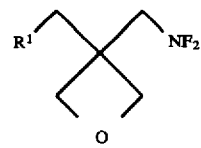

(II)

in which $R^1$ is a functional group including, but not limited to, H, lower alkyl, $NF_2$, $ONO_2$, $NO_2$, $N_3$ and $N(R^2)NO_2$ where $R^2$ is H or a lower alkyl, with nitric acid to form a product mixture; and (b) recovering the compound represented by Formula I from said product mixture.

Within the scope of the above process, certain embodiments are preferred, namely those in which $R^1$ of the starting material represented by Formula II is a functional groups selected from the following: H, $NF_2$, or $ONO_2$. More preferred are the embodiments in which $R^1$ of the starting material is either H or $NF_2$.

In a preferred embodiment, the solution of step (a) is an organic solution. A solution of the compound represented by Formula II in methylene chloride is the presently preferred solution. The nitric acid used in the above process should have a concentration of at least about 95%, with a concentration of about 98% to about 100% being preferred. Compounds prepared using the above process are recovered using standard methods and procedures known in the art.

Compounds corresponding to Formula I can be synthesized, for example, using mono- and bis-$NF_2$-oxetanes as starting materials. Reaction of the mono- and bis-$NF_2$-oxetanes with 100% nitric acid in methylene chloride gives a quantitative yield of the corresponding dinitrate esters. Mono-$NF_2$-oxetane gives 2-difluoroaminomethyl-2-methylpropane-1,3-diol dinitrate, an oil, and bis-$NF_2$-oxetane gives 2,2-bis(difluoroaminomethyl) propane-1,3-diol dinitrate, a solid. These difluoroneopentyl amine plasticizers may also be synthesized by direct fluorination of amine dinitrates or by fluorination of amine diols followed by nitration.

Additionally, a wide variety of high-energy neopentyl difluoroamino compounds can be prepared either: (1) by the direct fluorination of amine derivatives containing energetic groups; or (2) by first preparing $NF_2$ derivatives and then

TABLE I

Properties of Neopentyl-$NF_2$-Nitrate Plasticers*

| STRUCTURE | MONO-$NF_2$-TRINITRATE | DI-$NF_2$-DINITRATE | TRI-$NF_2$-NITRATE | TETRA-$NF_2$ |
|---|---|---|---|---|
| DENSITY (g/cc) | 1.652 | 1.589 / 1.800 (x-ray) | 1.526 | 1.464 |
| $\Delta H_r$ (Kcal/g) | -33.5 | -29.03 | -24.2 | -19.04 |
| $I_{sp}$ | 271.7 | 274.6 | 282.3 | 288.2 |

*All values are calculated except for the density of the di-$NF_2$-compound which also has a measured value The invention further resides in the preparation of compounds represented by Formula I, in which $R^1$ is a functional substituting these derivatives with energetic groups. Energetic groups which are useful as substituents in these neopentyl difluoroamino compounds include, but are not limited to, $NF_2$, $NO_2$, $ONO_2$, $N(R^4)NO_2$, where $R^4$ is H or a lower alkyl, and $N_3$. Examples of these compounds include, but are not limited to, the following: 2-difluoroaminomethyl-2-nitratomethylpropane- 1,3-diol dinitrate; tris(difluoroaminomethyl)ethanol nitrate; and tetrakis(difluoroaminomethyl) methane. Table II shows the structures of some additional high-energy difluoroneopentyl amine plasticizers and/or oxidizers that can be prepared using the methods of the present invention.

TABLE II

Mixed $NF_2$-Substituted Plasticizers and Oxidizers

[Structural diagrams of mixed NF2-substituted compounds]

The invention will be described in greater detail by way of specific examples. The following examples are offered for illustrative purposes, and are intended neither to limit or define the invention in any manner.

EXAMPLE I

This example illustrates the preparation and properties of 2-difluoroaminomethyl-2-methylpropane- 1,3-diol dinitrate.

A. Preparation of Ethyl Carbamate of 3-Aminomethyl-3-methyloxetane

A solution of 3-aminomethyl-3-methyloxetane (10.1 g, 0.10 mol) in 50 mL of water containing sodium hydroxide (8.07 g, 0.2 mol) was cooled to 0° C., and ethyl chloroformate (22.38 g, 0.2 mol) was added dropwise over 1 h at a rate such that the temperature of the mixture did not exceed 2° C. The mixture was stirred for an additional 1 h at 0° C., and then extracted with three portions of 100 mL of methylene chloride. The combined organic extracts were then dried over magnesium sulfate and the solvent was removed by evaporation to yield 17.6 g of the ethyl carbamate of 3-aminomethyl-3-methyloxetane, representing a 99% yield.

An analytical sample was prepared by distillation at 106°–108° C. and 0.25 mm pressure. IR (DRIFTS): 3325, 2965, 1703, 1543, 1249 cm$^{-1}$. NMR: $^1$H NMR 1.25 (t, J 7 Hz, 3 H), 1.30 (s, 3 H), 3.36 (d, J=6 Hz, 2 H), 4.14 (q, J=7 Hz, 2 H), 4.36 (d, J=6 Hz, 2 H), 4.47 (d, J=6 Hz, 2 H); $^{13}$C NMR 14.623, 21.824, 40.105, 47.480, 61.031, 80.136. Elemental analysis calculated for $C_8H_{15}NO_3$: C, 55.47, H, 8.73; N, 8.09. Found: C, 54.57; H, 8.45; N, 8.25.

B. Preparation of 3-Difluoroaminomethyl-3-methyloxetane

A mixture of 10% fluorine in nitrogen was passed at 150–250 mL/min through a solution of the ethyl carbamate of 3-aminomethyl-3-methyloxetane (17.32 g, 0.1 mole) in 170 mL of acetonitrile at –10° C. After 4.5 h when $^{19}$F NMR analysis showed that the mono-fluorinated material was consumed (–40 ppm), the fluorine flow was discontinued. The reaction mixture was purged with nitrogen for 10 minutes and added to ice water (1 L). The bottom organic layer was separated, diluted with 35 mL of methylene chloride, washed with water and 5% aqueous sodium bicarbonate solution, and dried over magnesium sulfate. The solvent was removed by evaporation to yield 13.1 g (96% yield) of crude 3-difluoroaminomethyl-3-methyloxetane.

An analytical sample was purified by distillation at 37° C. and 5 mm pressure. Differential thermal analysis (DTA) showed maximum decomposition at 215° C.; Bureau of Mines Impact Sensitivity >100 cm; NMR: $^1$H NMR 1.56 (s, 3 H), 3.74 (t, J=27.8 Hz, 2 H), 4.36 (d, J=6.0 Hz, 2 H), 4.56 (d, J=6.0 Hz, 2 H); $^{13}$C NMR 21.528, 37.303 (t, J=12.5 Hz), 71.377(t, J=5.6 Hz), 80.234; $^{19}$F NMR 57.49 (t, J=27.8 Hz); Elemental analysis calculated for $C_5H_9NOF_2$: C, 43.79, H, 6.62; Found: C, 44.05; H, 6.75.

C. Preparation of 2-difluoroaminomethyl-2-methylpropane- 1,3-diol dinitrate

A mixture of 3-difluoroaminomethyl-3-methyloxetane (1.015 g, 7.41 mmol) and 100% nitric acid (3.0 g, 47.6 mmol) in 15 mL of methylene chloride was stirred at ambient temperature for 72 h. The reaction was monitored by GLC and when 100% of the starting material had been consumed, 25 mL of water was added to the reaction mixture. The organic layer was separated and dried over magnesium sulfate. The solvent was removed by evaporation, leaving 1.28 g of 2-difluoroaminomethyl-2-methylpropane-1,3-diol dinitrate as an oil, representing a 71% yield.

Differential scanning calorimetry showed an onset of decomposition at 190° C., and a maximum at 220° C.; NMR: $^1$H NMR 1.26 (s, 3 H), 3.63 (t, J=28.0 Hz, 2 H), 4.45 (s, 4 H); $^{13}$C NMR 35.079, 67.904 (t, J=7.6 Hz), 73.279; $^{19}$F NMR 60.90 (t, J 28.0 Hz).

EXAMPLE II

This example illustrates the preparation and properties of 2,2-bis-(difluoroaminomethyl)propane-1,3-diol dinitrate.

A. Preparation of Di(ethylcarbamate) of 3,3-bis (aminomethyl)oxetane

A solution of 3,3-bis(aminomethyl)oxetane (69.7 g, 0.60 mol) in 350 mL of water containing sodium hydroxide (72.65 g, 1.8 mol) was cooled to 0° C., and ethyl chloroformate (201.4 g, 1.8 mol) was added dropwise over 2 h at a rate such that the temperature of the mixture did not exceed 2° C. The mixture was stirred for an additional 2 h at 0° C., and the product was extracted with 300 mL of methylene chloride. The organic layer was separated, dried over magnesium sulfate and evaporated to give 153.2 g of the di(ethyl carbamate) of 3,3-bis(aminomethyl)oxetane, representing a 98% yield.

An analytical sample was prepared by recrystallization from carbon tetrachloride, mp 96°–96.5° C. IR (Drifts): 3338, 2900, 1694, 1536, 1255, 1030 cm$^{-1}$; NMR: $^1$H NMR 1.23 (t, J=7 Hz, 6 H), 3.49 (d, J=6 Hz, 4 H), 4.10 (q, J=7 Hz, 4 H), 4.40 (s, 4 H); $^{13}$C NMR 14.591, 43.644, 44.447, 61.135, 77.303, 157.686; Elemental analysis calculated for $C_{11}H_{20}N_2O_5$: C, 50.76; H, 7.75; N, 10.76; Found: C, 50.51, H, 7.65; N, 10.69.

B. Preparation of 3,3-Bis(difluoroaminomethyl)oxetane

A mixture of 10% fluorine in nitrogen was passed at 100–200 mL/min through a solution of the di(ethyl carbamate) of 3,3-bis(aminomethyl)oxetane (6.51 g, 0.025 mole) in 100 mL of acetonitrile at –20° C. After 4.5 h when $^{19}$F NMR analysis showed that the mono-fluorinated material was consumed (–40 ppm), the fluorine flow was discontinued. The reaction mixture was purged with nitrogen for 10 minutes and added to ice water (1 L). The bottom organic layer was separated and diluted with 35 mL of methylene chloride, washed with water and 5% aqueous sodium bicarbonate solution, and dried over magnesium sulfate. The solvent was removed by evaporation to give 3.92 g (83% yield) of crude 3,3-bis(difluoroaminomethyl) oxetane, mp 43.5°–44.5° C. ($CH_2Cl_2$).

An analytical sample was purified by sublimation at 50°–60° C. and 0.05 mm pressure. Differential scanning calorimetry (20° C./min, nitrogen) showed an onset of decomposition at 208° C., and a maximum at 230.8° C.; Bureau of Mines Impact Sensitivity >100 cm; NMR: $^1$H NMR 4.00 (t, J=28.0 Hz, 4 H), 4.60 (s, 4 H); $^{13}$C NMR 39.490, 67.398 (t, J=7.5 Hz), 77.230 (t, J=14.9 Hz); $^{19}$F NMR 56.37 (t, J=27.8 Hz); Elemental analysis calculated for $C_5H_8N_2OF_4$: C, 31.92; H, 4.29; N, 14.89; Found: C, 31.58; H, 4.17; N, 14.73.

C. Preparation of 2,2-Bis(difluoroaminomethyl)propane-1,3-diol dinitrate

A mixture of 3,3-bis(difluoroaminomethyl)oxetane (2.89 g, 15.4 mmol) and 100% nitric acid (3.0 g, 47.6 mmol) in 15 mL of methylene chloride was stirred at ambient temperature for 7 days. The reaction was monitored by gas-liquid chromatography (GLC) and when 90% of the starting material had been consumed, 25 mL of water was added. The organic layer was separated and dried over magnesium sulfate. The solvent was removed by evaporation. The remaining solid residue was recrystallized from hexanes/methylene chloride to give 2.46 g of 2,2-bis(difluoroaminomethyl) propane-1,3-diol dinitrate, representing a 54% yield, MP: 57.90° C.

Differential scanning calorimetry showed an onset of decomposition at 176.6° C., and a maximum at 187.7° C.; Heat Flow: 3618 Joules/g; Bureau of Mines Impact Sensitivity 13.7 cm (50%), 12.8–14.5 cm (95%); NMR: $^1$H NMR 3.83 (t, J=27.6 Hz, 4 H), 4.61 (s, 4 H); $^{13}$C NMR 39.490, 65.066 (t, J=8.6 Hz), 69.753; $^{19}$F NMR 61.90 (t, J=27.6 Hz); Elemental analysis calculated for $C_5H_8N_4O_6F_4$: C, 20.28; H, 2.72; N, 18.92; Found: C, 20–58; H, 2.65; N, 18.78.

The foregoing is offered primarily for purposes of illustration. It will be readily apparent to those skilled in the art that the operating conditions, materials, procedural steps and other parameters of the systems described herein may be further modified or substituted in various ways without departing from the spirit and scope of the invention.

What is claimed is:

1. A compound having the formula

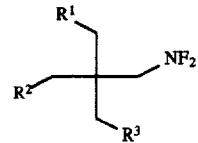

in which either:

$R^1$, $R^2$ and $R^3$ are members independently selected from the group consisting of H, lower alkyl, $NF_2$, $ONO_2$, $NO_2$, $N_3$ and $N(R^4)NO_2$ where $R^4$ is H or a lower alkyl; or:

$R^1$ and $R^2$ are combined as a single divalent radical which is a member selected from the group consisting of —N($NO_2$)— and —N($NO_2$)—$CH_2$—N($NO_2$)—; and $R^3$ is a member selected from the group consisting of $NF_2$, $ONO_2$, $NO_2$ and $N_3$.

2. A compound in accordance with claim 1 in which either:

$R^1$, $R^2$ and $R^3$ are members independently selected from the group consisting of H, $CH_3$, $C_2H_5$, $NF_2$, $ONO_2$, $NO_2$, $N_3$, $N(CH_3)NO_2$ and $N(C_2H_5)NO_2$; or:

$R^1$ and $R^2$ are combined as a single divalent radical which is a member selected from the group consisting of —N($NO_2$)— and —N($NO_2$)—$CH_2$—N($NO_2$)—; and $R^3$ is a member selected from the group consisting of $NF_2$, $ONO_2$, $NO_2$ and $N_3$.

3. A compound in accordance with claim 1 in which $R^1$, $R^2$ and $R^3$ are members independently selected from the group consisting of H, $NF_2$, $ONO_2$, $NO_2$, $N_3$ and $N(CH_3)NO_2$.

4. A compound in accordance with claim 1 in which $R^1$, $R^2$ and $R^3$ are members independently selected from the group consisting of H, $NF_2$ and $ONO_2$.

5. A compound in accordance with claim 1 in which $R^1$ is a member selected from the group consisting of H and $NF_2$, $R^2$ is $ONO_2$, and $R^3$ is $ONO_2$.

6. A process for the preparation of a compound having the formula

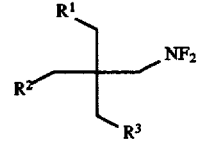

in which $R^1$ is a member selected from the group consisting of H, lower alky, $NF_2$, $ONO_2$, $NO_2$, $N_3$, $N(R^4)NO_2$, where $R^4$ is H or a lower alkyl; $R^2$ is $ONO_2$; and $R^3$ is $ONO_2$, said process comprising:

(a) combining a solution of a compound having the formula

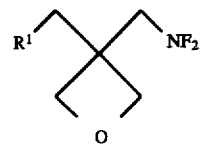

in which $R^1$ is a member selected from the group consisting of H, lower alkyl, $NF_2$, $ONO_2$, $NO_2$, $N_3$, $N(R^2)NO_2$, where $R^2$ is H or a lower alkyl, with nitric acid to form a product mixture; and (b) recovering compound II from said product mixture.

7. A process in accordance with claim 6 in which $R^1$ is a member selected from the group consisting of H, $NF_2$ and $ONO_2$.

8. A process in accordance with claim 6 in which $R^1$ is a member selected from the group consisting of H and $NF_2$.

9. A process in accordance with claim 6 in which said nitric acid has a concentration of at least 95%.

10. A process in accordance with claim 6 in which said solution of step (a) is an organic solution.

* * * * *